US012558290B2

(12) United States Patent
Hsu et al.

(10) Patent No.: US 12,558,290 B2
(45) Date of Patent: Feb. 24, 2026

(54) BLOOD PRESSURE LOWERING TRAINING DEVICE

(71) Applicants: METABRAIN TECHNOLOGY PTE. LTD., Singapore (SG); ZHUHAI ULOOK METABRAIN MEDICAL TECHNOLOGY CO., LTD., Zhuhai City (CN)

(72) Inventors: Chen-Chao Hsu, Taichung City (TW); Shin-Da Lee, Taichung (TW); Yi-Yuan Lin, Taipei City (TW); Cheng-Ju Wu, Changhua County (TW)

(73) Assignees: METABRAIN TECHNOLOGY PTE. LTD., Singapore (SG); ZHUHAI ULOOK METABRAIN MEDICAL TECHNOLOGY CO., LTD., Zhuhai City (CN)

( * ) Notice: Subject to any disclaimer, the term of this patent is extended or adjusted under 35 U.S.C. 154(b) by 804 days.

(21) Appl. No.: 17/896,373

(22) Filed: Aug. 26, 2022

(65) Prior Publication Data

US 2023/0062659 A1     Mar. 2, 2023

(30) Foreign Application Priority Data

Aug. 27, 2021    (TW) ................................. 110131808

(51) Int. Cl.
| | |
|---|---|
| *A61H 39/04* | (2006.01) |
| *A43B 7/1455* | (2022.01) |
| *A61B 5/021* | (2006.01) |
| *A61H 39/00* | (2006.01) |

(52) U.S. Cl.
CPC ............. *A61H 39/04* (2013.01); *A43B 7/146* (2013.01); *A61B 5/02141* (2013.01); *A61H 39/002* (2013.01); *A61H 2201/10* (2013.01)

(58) Field of Classification Search
CPC .. A61H 39/04; A61H 39/002; A61H 2201/10; A43B 7/146; A43B 5/02141; A61B 5/02141
See application file for complete search history.

(56) References Cited

U.S. PATENT DOCUMENTS

| | | | | |
|---|---|---|---|---|
| 2007/0106169 A1* | 5/2007 | Fadem | ................... | A61B 5/374 |
| | | | | 600/383 |
| 2010/0239096 A1* | 9/2010 | Jeon | ......................... | H04R 3/04 |
| | | | | 381/1 |
| 2014/0228721 A1* | 8/2014 | Ehrenreich | ........ | A61H 23/0245 |
| | | | | 601/47 |

(Continued)

*Primary Examiner* — Jack Yip
(74) *Attorney, Agent, or Firm* — MUNCY, GEISSLER, OLDS & LOWE, P.C.

(57) ABSTRACT

A blood pressure lowering training device comprises a head frame unit corresponding to a user's head shape, an audio stimulation unit for broadcasting binaural beats with frequency following response to both ears of the user, a display unit including a display module for displaying a virtual image and blood pressure information and a blood pressure measurement module for measuring blood pressure, and a control unit electrically connected with the audio stimulation unit and the display unit, so that the hypertensive patient can perform a variety of adjustable blood pressure lowering training in one use process, and effectively improve the use intention of the hypertensive patient.

18 Claims, 12 Drawing Sheets

(56)　　　　　　References Cited

U.S. PATENT DOCUMENTS

| | | | |
|---|---|---|---|
| 2015/0005568 A1* | 1/2015 | Chib | A61N 2/006 |
| | | | 607/45 |
| 2015/0313496 A1* | 11/2015 | Connor | A61B 5/369 |
| | | | 600/301 |
| 2016/0007918 A1* | 1/2016 | Badower | A61B 5/6803 |
| | | | 600/383 |
| 2018/0133507 A1* | 5/2018 | Malchano | A61N 1/36082 |
| 2023/0066359 A1* | 3/2023 | Yang | A61N 5/0618 |
| 2024/0172949 A1* | 5/2024 | Jumbe | A61B 5/6814 |

* cited by examiner

BLOOD PRESSURE LOWERING TRAINING DEVICE

BACKGROUND OF THE INVENTION

Field of the Invention

The present invention relates to a training device, in particular to a blood pressure lowering training device.

Description of the Prior Art

Generally, hypertensive patients usually take drugs to control their blood pressure, while another way to control their blood pressure is to require hypertensive patients to exercise. However, for some hypertensive patients, they are often reluctant to take the initiative to exercise because they don't have exercise habits.

Therefore, it is necessary to develop equipment to make hypertensive patients willing to exercise.

SUMMARY OF THE INVENTION

Therefore, it is an object of the present invention to provide a blood pressure lowering training device that overcomes the disadvantages described in the prior art.

Therefore, the blood pressure lowering training device of the present invention includes a head frame unit, an audio stimulation unit, a display unit, and a control unit.

The head frame unit corresponds to a user's head shape, and includes two ears corresponding to both ears of the user, a top-side portion connected between the ears and spanning the user's head.

The audio stimulation unit includes two speakers arranged at the ears, and the speakers are used to broadcast binaural beats with frequency following response to both ears of the user, and the binaural beats has a frequency difference.

The display unit includes a display module arranged on the front-side of the head frame unit to display a virtual image for the user's eyes, a blood pressure measurement module for measuring the user's blood pressure and outputting the measurement result by signal. The display module can also display the blood pressure information measured by the blood pressure measurement module.

The control unit is electrically connected with the speakers and the display unit, stores the digital information of the binaural beats with frequency following response, and can control the speakers to broadcast the binaural beats with frequency following response according to a preset command, and change the virtual image in the display module.

The effect of the present invention lies in that by setting the speakers that can broadcast the binaural beats with frequency following response, and the display module that can display the virtual image and blood pressure information, the hypertensive patient can perform a variety of adjustable blood pressure lowering exercises in one use process, effectively enhancing the use intention of the hypertensive patient.

BRIEF DESCRIPTION OF THE DRAWINGS

Other features and effects of the present invention will appear clearly in the embodiments with reference to the drawings, in which.

DETAILED DESCRIPTION OF THE PREFERRED EMBODIMENTS

Figure 1:
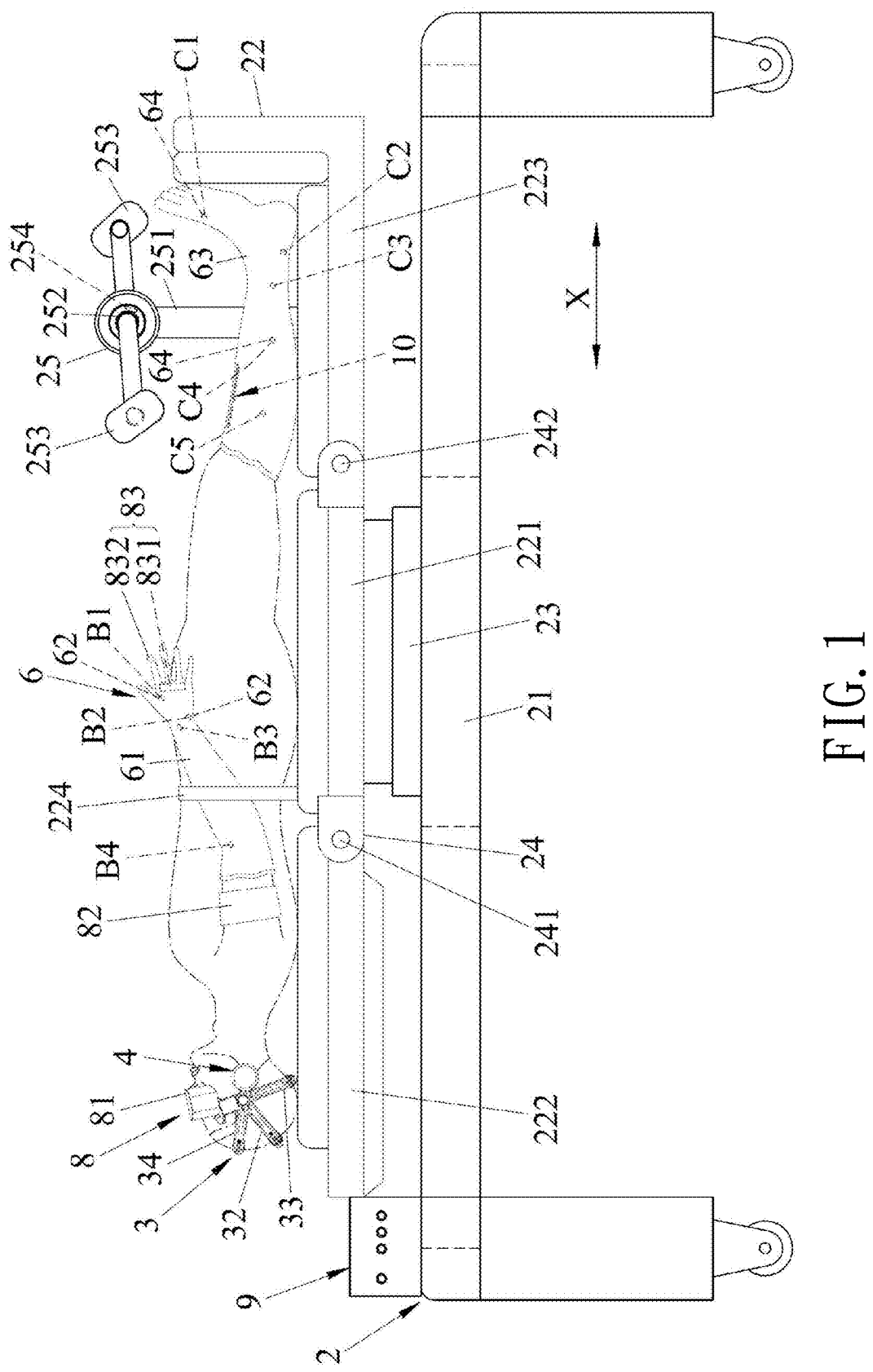
FIG. 1 is a side view of an embodiment of the blood pressure lowering training device of the present invention, illustrating the state of a user lying flat.
Figure 2:
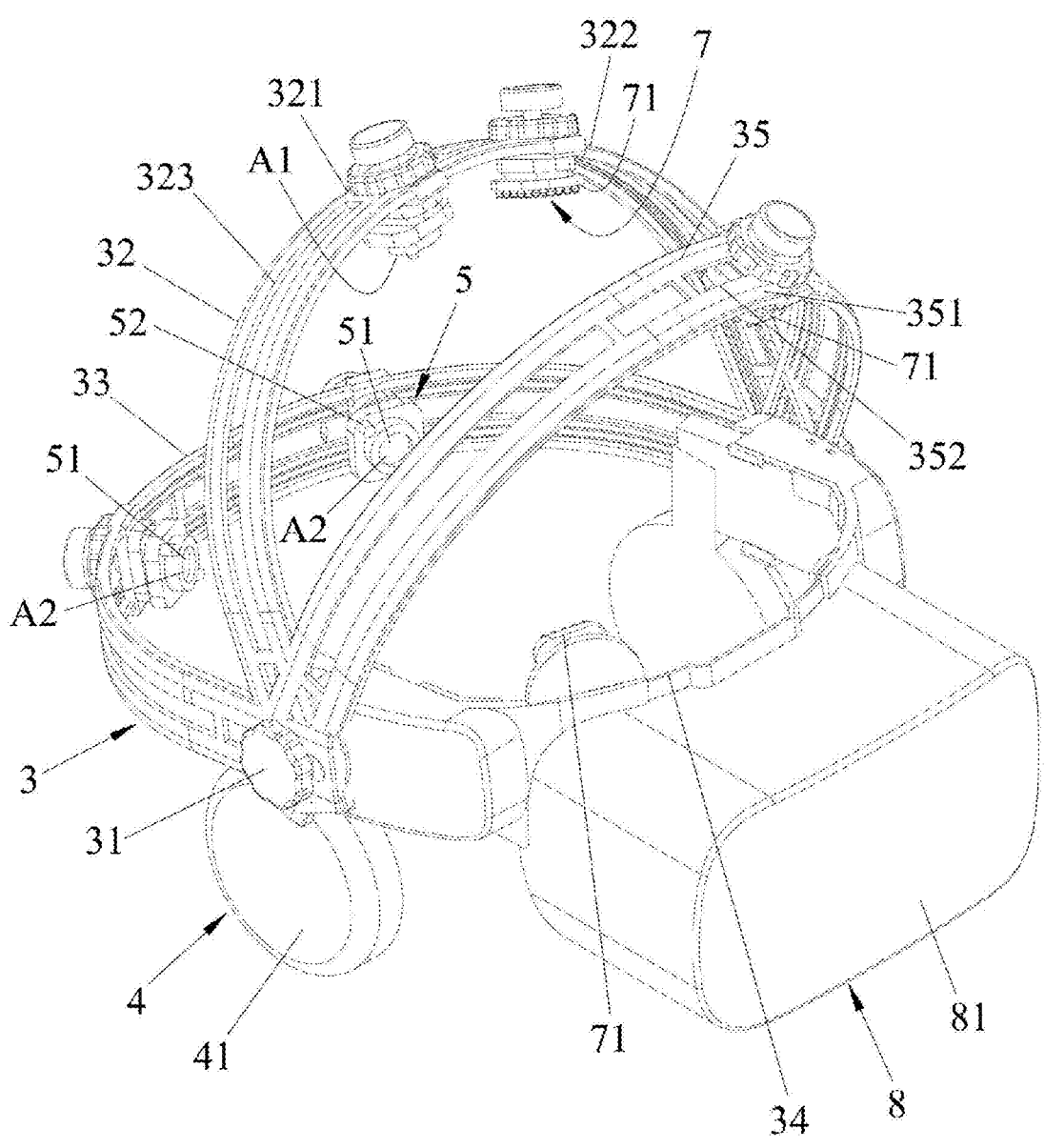
FIG. 2 is a perspective view of a head frame unit, an audio stimulation unit, a head acupoint stimulation unit and an electronic stimulation unit in this embodiment.
Figure 3:
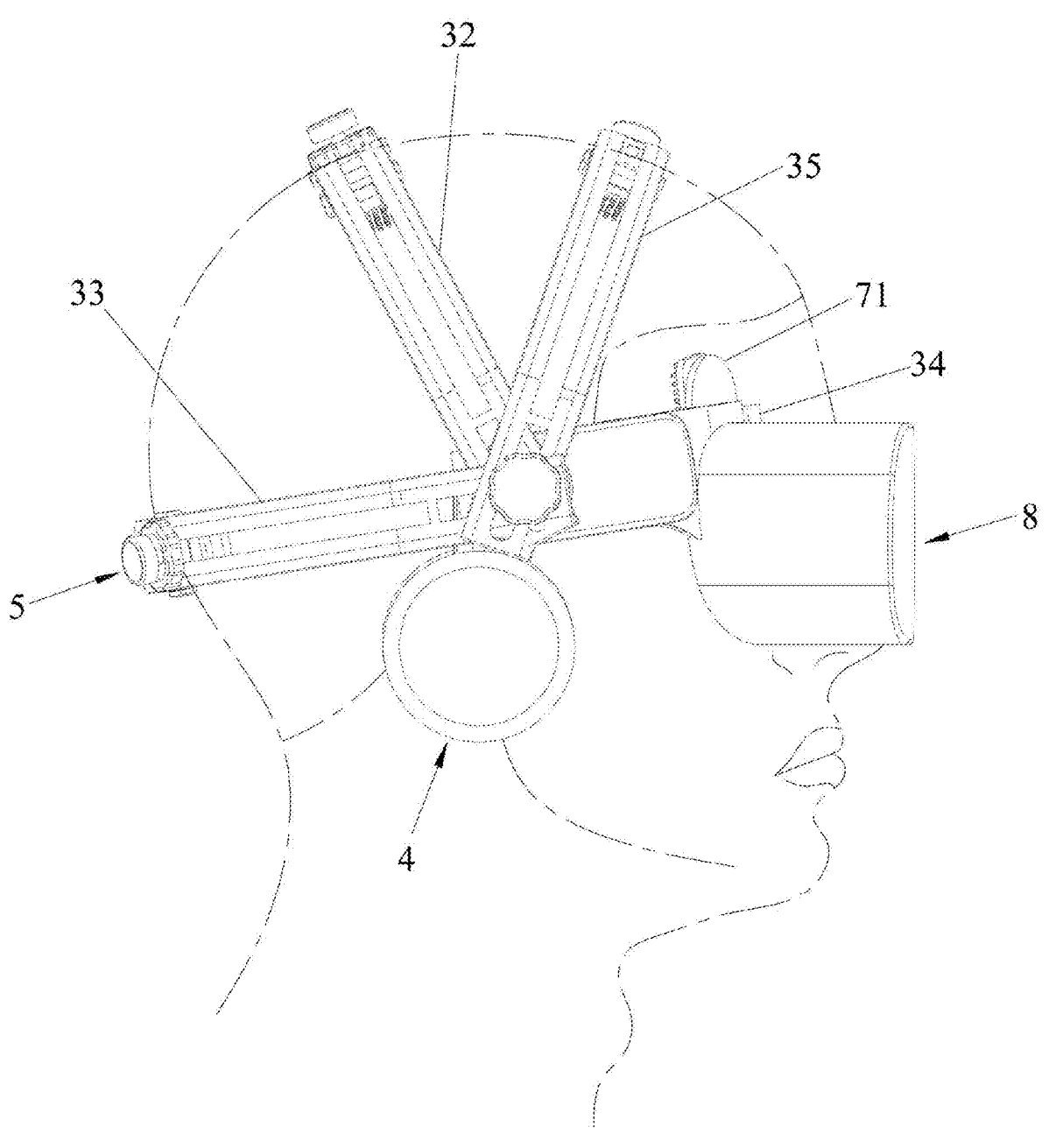
FIG. 3 is a side view of the head frame unit, the audio stimulation unit, the head acupoint stimulation unit and the electronic stimulation unit in this embodiment.

Referring to FIGS. 1, 2, and 3, an embodiment of the blood pressure lowering training device of the present invention comprises a rhythmic bed unit 2, a head frame unit 3, an audio stimulation unit 4, a head acupoint stimulation unit 5, a limb acupoint stimulation unit 6, an electronic stimulation unit 7, a display unit 8, a control unit 9, and a phototherapeutic unit 10.

The rhythmic bed unit 2 includes a base 21, a bed module 22 arranged on the base 21, a periodic acceleration module 23 that is arranged between the base 21 and the bed module 22 and can perform periodic acceleration motion, a driving module 24 arranged on the bed module 22, and a pedal module 25 arranged on the bed module 22.

The bed module 22 has a middle portion 221 disposed above the base 21, an upper body portion 222 swingably disposed on the head-side of the middle portion 221 along a head-foot direction X, and a swingable upper body portion 222 along the head-foot direction X is arranged on the lower body portion 223 at the foot-side of the middle portion 221, and a fixed waist belt 224 is arranged on the middle portion 221.

The periodic acceleration module 23 is arranged between the base 21 and the middle portion 221, and can be controlled to drive the middle portion 221 to move back and forth along the head-foot direction X. In this embodiment, the periodic acceleration motion is a process of driving the middle portion 221 to move horizontally back and forth along the head-foot direction X for a predetermined time.

The driving module 24 has a first driving member 241 arranged between the middle portion 221 and the upper body portion 222 and controlled to drive the upper body portion 222 to swing relative to the middle portion 221, and a second driving member 242 arranged between the middle portion 221 and the lower body portion 223 and controlled to drive the lower body portion 223 to swing relative to the middle portion 221. In this embodiment, the swing angle at which the first driving member 241 can drive the upper body portion 222 to swing relative to the middle portion 221 is between a horizontal upward 90 degrees angle and a horizontal downward 45 degrees angle. The swing angle at which the second driving member 242 can drive the lower body portion 223 to swing relative to the middle portion 221 is between a horizontal upward 45 degree angle and a horizontal downward 45 degree angle.

In this embodiment, the periodic acceleration module 23, the first driving member 241 and the second driving member 242 are composed of a motor and a transmission mechanism, which are not the main technical features of the present invention, so this description will not further explain them.

The pedal module 25 has a supporting portion 251 arranged on the lower body portion 223, a crank 252 pivoted on the supporting portion 251, two pedals 253 respectively arranged on two opposite sides of the crank 252, and a sensor 254 arranged on the crank 252 and outputting the rotation of the crank 252 as a sensing signal. In this embodiment, the sensor 254 is a rotational speed sensor, and the sensing signal corresponds to the rotational speed of the crank 252.

Figure 4:
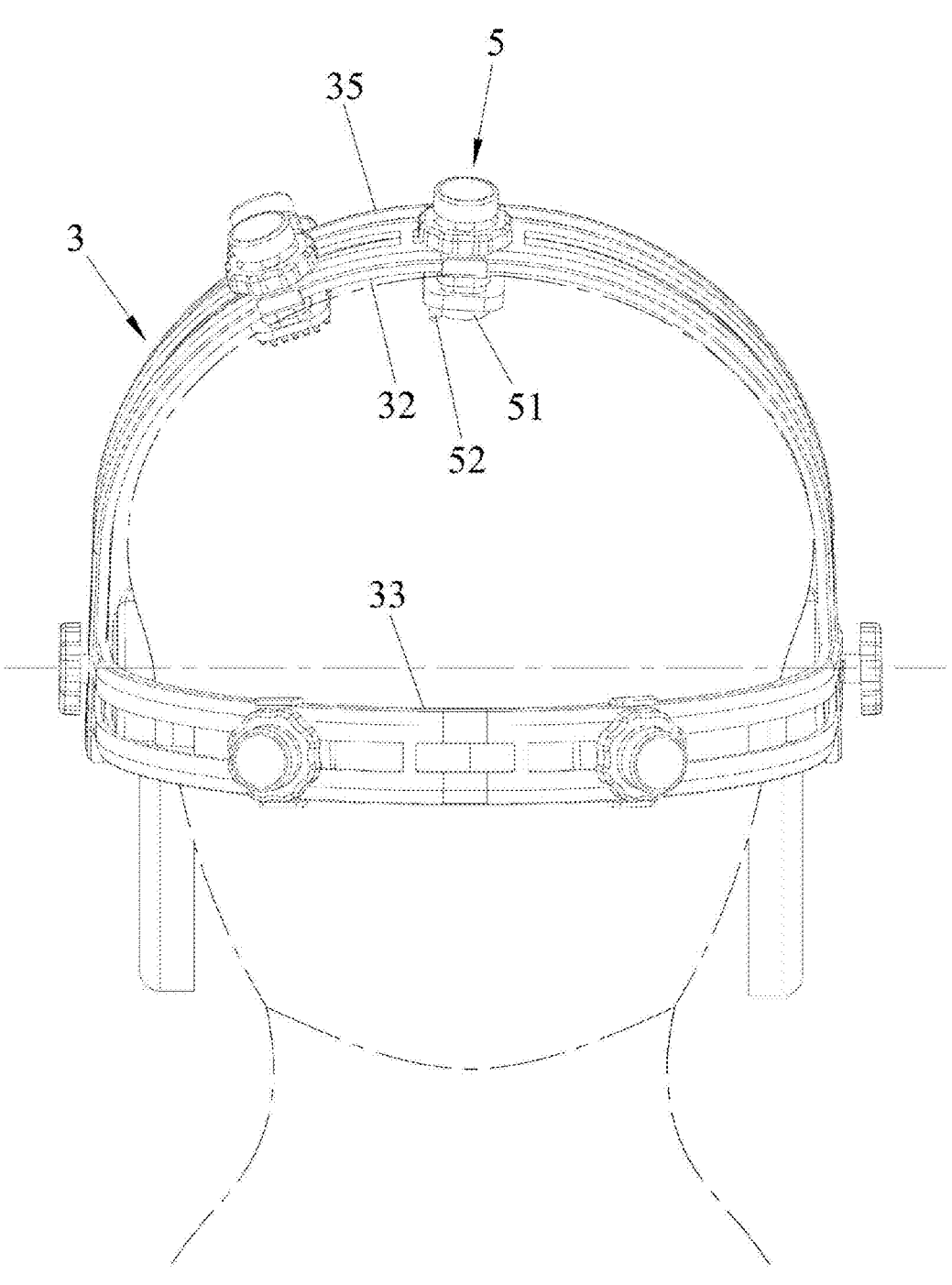
FIG. 4 is a rear view of the head frame unit, the audio stimulation unit, the head acupoint stimulation unit and the electronic stimulation unit in this embodiment.

Referring to FIGS. 2, 3 and 4, the head frame unit 3 corresponds to a user's head shape, and includes two ears 31 corresponding to both ears of the user, a top-side portion 32 connected between the ears 31 and spanning the user's head, a back-side portion 33 connected between the ears 31 and spanning the user's back skull, and a front-side portion 34 connected between the ears 31 and spanning the user's forehead and a middle portion 35 connected between the ears 31 and located between the top-side portion 32 and the front-side portion 34.

Figure 5:
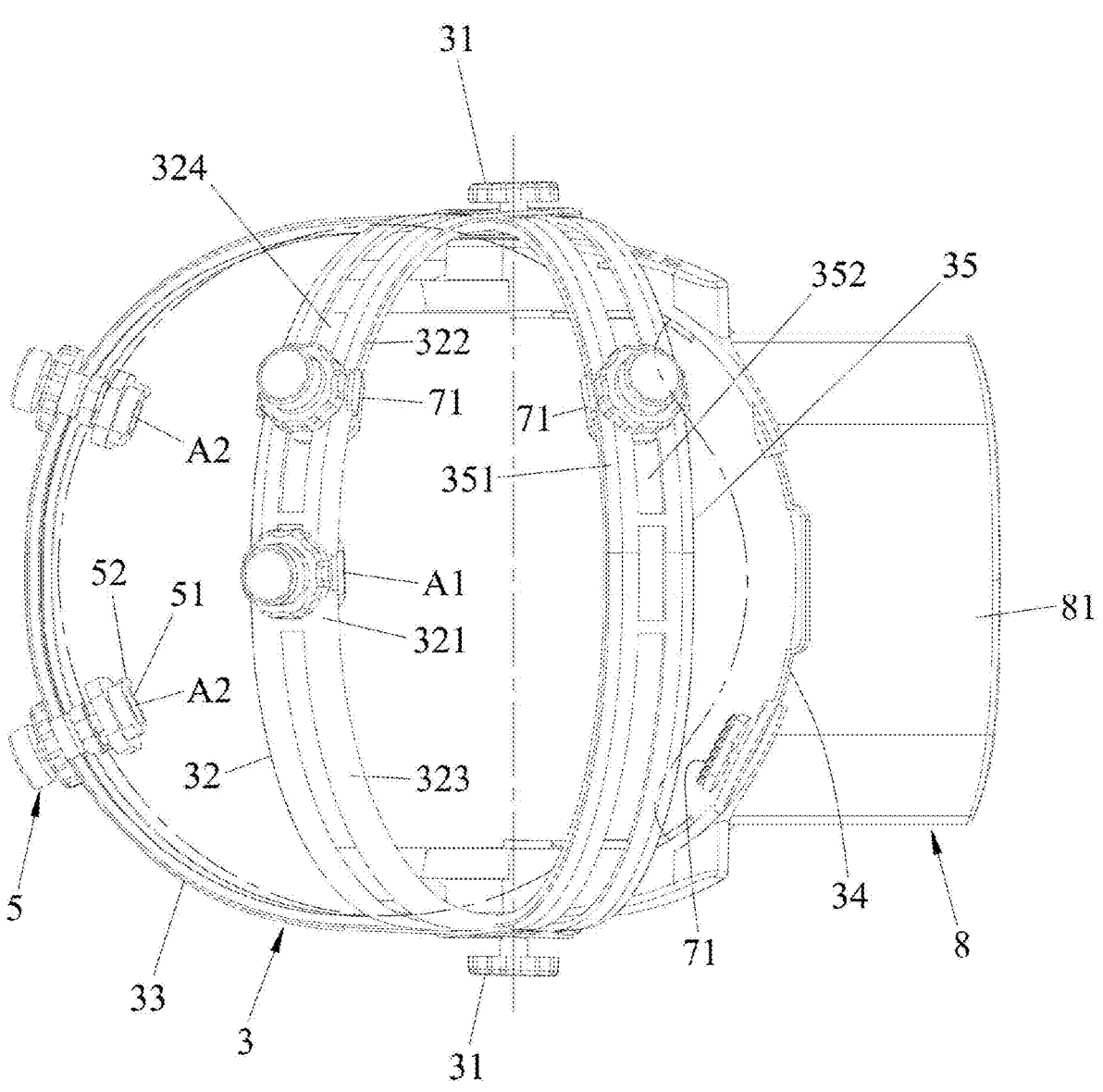
FIG. 5 is a plan view of the head frame unit, the audio stimulation unit, the head acupoint stimulation unit and the electronic stimulation unit in this embodiment.

Referring to FIGS. 2, 3 and 5, the top-side portion 32 has a top area 321 located at the center between the ears 31, a left area 322 and a right area 323 connected between the ears 31 and the top area 321, and a first mounting slot 324 located in the left area 322, the middle portion 35 has a left front area 351 corresponding to the left area 322 and a second mounting slot 352 located in the left front area 351.

The audio stimulation unit 4 includes two speakers 41 arranged at the ears 31, and the speakers 41 are used to broadcast binaural beats with frequency following response to both ears of the user, and the binaural beats with frequency following response has a frequency difference. In this embodiment, the frequency difference of the binaural beats with frequency following response is from 14 Hz to 4 Hz.

Figure 6:
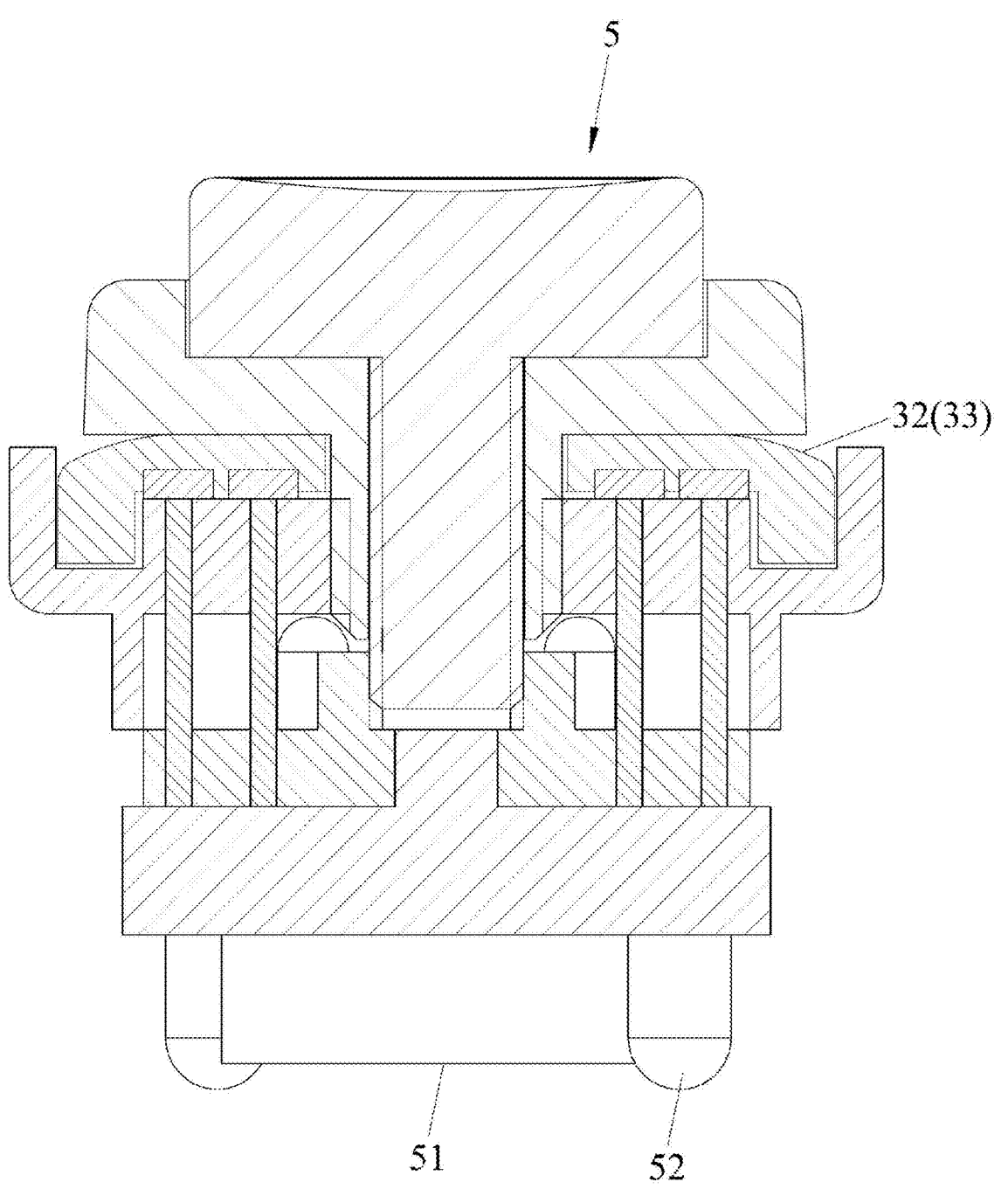
FIG. 6 is an incomplete sectional schematic diagram of the head acupoint stimulation unit of this embodiment.

Referring to FIGS. 3, 5 and 6, the head acupoint stimulation unit 5 includes three head acupoint agents 51 arranged in the head frame unit 3, and three resistance measurement medium 52 adjacent to the head acupoint agents 51, respectively. The head acupoint agents 51 are used to output the physical stimulation of laser light to the user's head acupoint. In this embodiment, the wavelength of the laser light of the head acupoint agents 51 is between 500 nm and 900 nm, and each resistance measuring medium 52 is used to measure the body resistance of the user to confirm whether the corresponding head acupoint agents 51 is located in a low resistance acupoint area.

Referring to FIGS. 3, 4 and 5, one of the head acupoint agents 51 is adjustably arranged in the center of the top area 321 to correspond to Baihui acupoint (international acupoint code GV20) of the user, which is indicated by the number A1 in the figure.

Two of the head acupoint agents 51 are adjustably arranged on the back-side portion 33, located seven times rearward of the center of the top area 321, and separated by 2.25 times of the finger distance toward the ears 31 to correspond to two Fengchi acupoints (international acupoint code GB20) of the user respectively, which are indicated by the number A2 in the figure. In this embodiment, the finger distance is substantially 2.3 cm.

Referring to FIG. 1, the limb acupoint stimulation unit 6 includes a glove 61, four hand acupoint agents 62 disposed on the glove 61, a foot cover 63, and five foot acupoint agents 64 disposed on the foot cover 63.

The hand acupoint agents 62 and the foot acupoint agents 64 are respectively used to output physical stimulation of laser light to the user's hand acupoint and foot acupoint. In this embodiment, the laser wavelengths of the hand acupoint agents 62 and the foot acupoint agents 64 are between 500 nm to 900 nm.

One of the hand acupoint agents 62 can adjustably correspond to Hegu acupoint (international acupoint code LI4) of the user, which is indicated by B1 in the figure, and one of the hand acupoint agents 62 can adjustably correspond to Shenmen acupoint (international acupoint code HT7) of the user, which is indicated by B2 in the figure. One of the hand acupoint agents 62 can adjustably correspond to the user's Neiguan acupoint (international acupoint code PC6), which is indicated by B3 in the figure, and one of the hand acupoint agents 62 can adjustably correspond to the user's Quchi acupoint (international acupoint code LI11), which is indicated by B4 in the figure.

One of the foot acupoint agents 64 can adjustably correspond to the user's Taichong acupoint (international acupoint code LR3), which is indicated by C1 in the figure, and one of the foot acupoint agents 64 can adjustably correspond to the user's Taixi acupoint (international acupoint code KI3), which is indicated by C2 in the figure. One of the foot acupoint agents 64 can adjustably correspond to the user's Sanyinjiao acupoint (international acupoint code SP6), which is indicated by C3 in the figure, one of the foot acupoint agents 64 can adjustably correspond to the user's Fenglong acupoint (international acupoint code ST40), which is indicated by C4 in the figure, and one of the foot acupoint agents 64 can adjustably correspond to the user's Zusanli acupoint (international acupoint code ST36).

Referring to FIGS. 1, 2 and 6, it should be explained that the above-mentioned method of corresponding user's acupoints is to measure the resistance of human skin near the acupoints, take the lowest resistance as the position of the acupoints, and then fine-tune the corresponding acupoints medium 51, 62 and 64 to correspond to the corresponding positions to complete the positioning of the acupoints. In this embodiment, the positioning of the head acupoint agents 51 is to measure the resistance through the resistance measuring medium 52.

Figure 7:
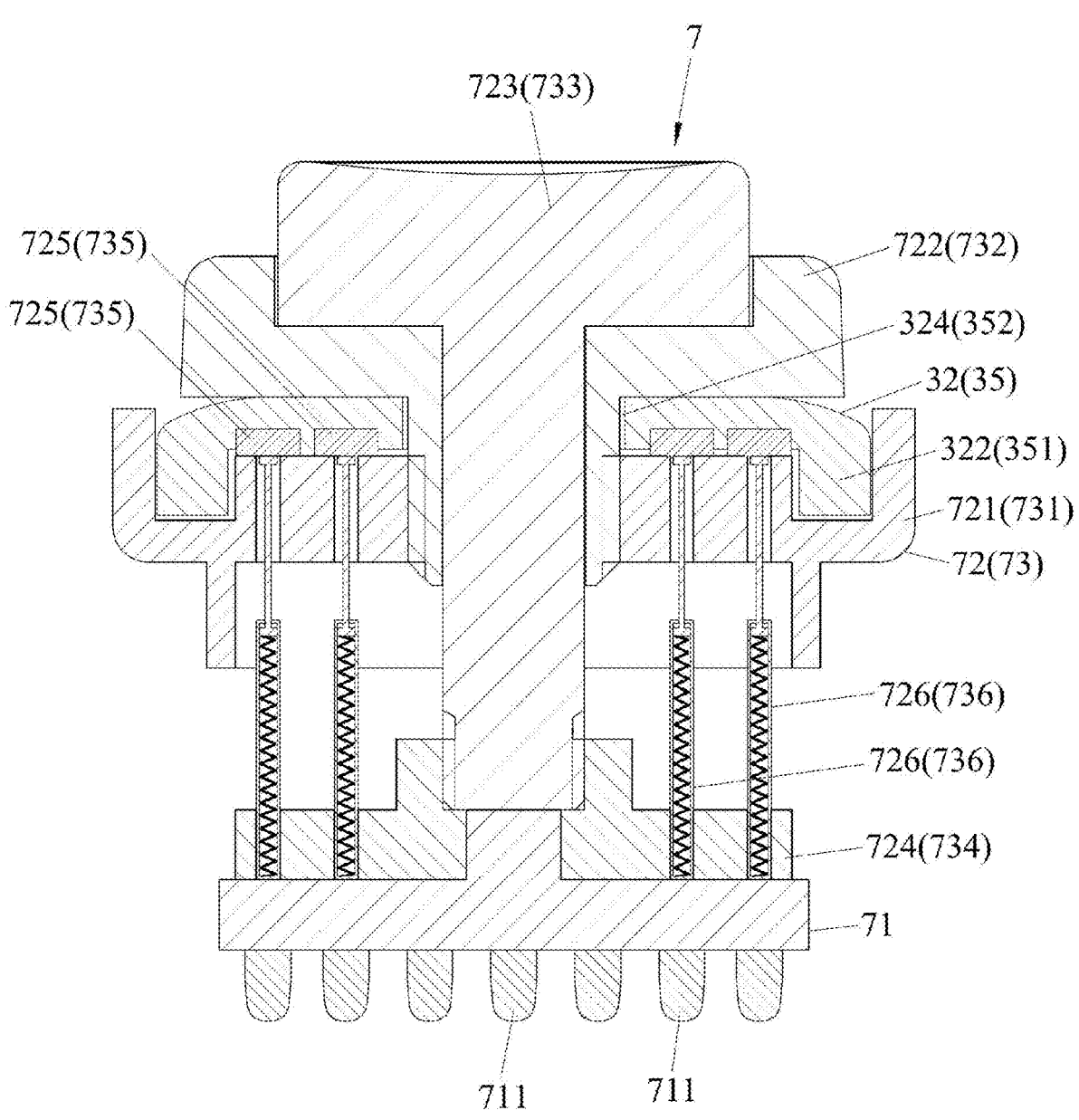
FIG. 7 is a schematic cross-sectional view of the electronic stimulation unit of this embodiment.

Referring to FIGS. 2, 5 and 7, the electrical stimulation unit 7 includes three electronical stimulation agents 71, a first setting base 72 and a second setting base 73, which respectively correspond to the left area 322, the left front area 351 and the front-side portion 34.

The electronical stimulation agents 71 correspond to the left side area 322, the left front area 351 and the front-side portion 34, respectively, corresponding to the C3 position in the international 10-20 electroencephalogram electrode position (that is, the position of the electronical stimulation agents 71 disposed in the left side area 322 in the figure), F3 (i.e., the position of the electronical stimulation agents 71 in the left front area 351 in the figure) and SO (i.e., the position of the electronical stimulation agents 71 in the front-side portion 34 in the figure), and are used for physical stimulation of one of outputting current to the user's head for transcranial electrical stimulation and outputting electromagnetic pulse for transcranial magnetic stimulation.

The first setting base 72 has a first sliding member 721 installed at the bottom of the top-side portion 32, a first screw locking member 722 passing through the first mounting slot 324 from the side opposite to the top-side portion 32 and screwed to the first sliding member 721 for fixing the first sliding member 721, a side of the first sliding member 721 opposite to the first screw locking member 722 slidably passes through the first positioning member 723 of the first screw locking member 722, a first mounting platform 724 arranged on the side of the first sliding member 721 opposite to the top-side portion 32 and screwed to the first positioning member 723, two first conductive strips 725 arranged at the bottom of the top-side portion 32, And two first elastic conductive members 726 that can compressively pass through the first sliding member 721 and the first mounting platform 724 and electrically connect the first conductive strips 725, respectively. The electronical stimulation agents 71 corresponding to the left side region 322 is disposed on the side of the first mounting platform 724 opposite to the top-side portion 32 and electrically connects the first elastic conductive member 726.

The second setting base 73 has a second sliding member 731 installed at the bottom of the middle portion 35, a second screw locking member 732 that passes through the second mounting slot 352 from the side opposite to the middle portion 35 and is screwed to the second sliding member 731 for fixing the second sliding member 731, A second positioning member 733 of the second sliding member 731 from the opposite side of the second screw locking member 732 slidably passes through the second positioning member 733 of the second screw locking member 732, a second mounting platform 734 arranged on the opposite side of the second sliding member 731 to the middle portion 35 and screwed to the second positioning member 733, two second conductive strips 735 arranged at the bottom of the middle portion 35, And two second elastic conductive members 736 that can compressively pass through the second sliding member 731 and the second mounting platform 734 and electrically connect the second conductive strips 735, respectively. The electronical stimulation agents 71 corresponding to the left front area 351 is disposed on the side of the second mounting platform 734 opposite to the middle portion 35 and electrically connects the second elastic conductive members 736.

In this embodiment, the physical stimulation is direct current of transcranial direct current stimulation (tDCS), with a current of 1 mA to 2 mA and a current density of 0.03 mA/cm$^2$ to 0.09 mA/cm$^2$, but it is not limited to this. It can also be an electromagnetic pulse for transcranial magnetic stimulation (TMS), with an electromagnetic frequency of substantially 1 Hz. Two of these electronical stimulation agents 71, which respectively correspond to the C3 position and F3 position in the international 10-20 electroencephalogram electrode position, are anodes, and one of these electronical stimulation agents 71, which corresponds to the SO position in the international 10-20 electroencephalogram electrode position, is cathodes.

Each electronical stimulation agents 71 has several conductive pillars 711 arranged in parallel to output physical stimulation.

Referring to FIGS. 1, 2 and 5, the display unit 8 includes a display module 81 arranged on the front-side 34 of the head frame unit 3 to display a virtual image for the user's eyes, a blood pressure measurement module 82 for measuring the user's blood pressure and outputting the measurement result by signal, and a pulse wave transit time monitoring module 83 for measuring the user's pulse transit time (PTT). In this embodiment, the virtual image is a VR image, and the blood pressure measurement module 82 is an electronic sphygmomanometer that can be sleeved on the upper arm of the user. The pulse wave transit time monitoring module 83 can simultaneously measure the heart rate (HR) by holding a heart rate sensor 831 in the hand and wear a light volume sensor 832 on the finger distance to measure the photoplethysmogram (PPG) of the index finger, to calculate the pulse wave transit time, and then displaying the blood pressure information measured by the blood pressure measuring module 82 and the calculated pulse wave transit time on the display module 81, and displaying the method that can make the user relax, so that the user can evaluate the changes of autonomic nerve and cardiovascular system according to the measured self-physiological feedback signal, and use it for self-adjusting physiological conditions.

Figure 8:
FIG. 8 is a display schematic diagram of a display module of this embodiment.

The display unit 8 can be switched between a display mode and an optical frequency-flashed stimulation mode. When in the display mode, the display module 81 displays the virtual image for the user's eyes. In the optical frequency-flashed stimulation mode, the display module 81 stimulates the user's eyes with a flickering picture. When in the optical frequency-flashed stimulation mode, the flickering picture displayed by the display module 81 flickers with no ultraviolet blue light with a wavelength between 450 nm and 465 nm. In this embodiment, the display mode and the optical frequency-flashed stimulation mode can also be executed simultaneously. Referring to FIGS. 1 and 8, the flickering picture displayed by the display module 81 refers to the rectangular flickering light 811 located at the outer frame of the virtual image, but it is not limited to this.

Referring to FIGS. 1, 2 and 5, the control unit 9 is electrically connected to the periodic acceleration module 23, driving module 24, the sensor 254, the speakers 41, the head acupoint agents 51, the resistance measurement medium 52, the hand acupoint agents 62, the foot acupoint agents 64, the electronical stimulation agents 71 and the display unit 8, and stores the binaural beats with frequency following response. According to a preset command, the periodic acceleration module 23 can be controlled to perform periodic acceleration movement, the driving module 24 drives the upper body portion 222 and the lower body portion 223 to swing, the speakers 41 broadcast the binaural beats with frequency following response, the head acupoint agents 51 emit physical stimulation, the hand acupoint agents 62 emit physical stimulation, the foot acupoint agents 64 emit physical stimulation, and the electronical stimulation agents 71 emit physical stimulation. And receiving and changing the virtual image in the display module 81 according to the sensing signal or the measurement result of the self-physiological feedback signal measured by the blood pressure measurement module 82 and the pulse wave transit time monitoring module 83. In this embodiment, the digital information, the virtual image, the preset command, and the content of displaying the method that enables the user to relax are downloaded through the cloud network and then pre-stored in the control unit 9.

The phototherapeutic unit 10 is arranged on the foot cover 63, and is used for emitting no ultraviolet flashing blue light with a wavelength between 450 nm and 465 nm to the user. In this embodiment, the phototherapeutic unit 10 is an LED. In other embodiments, the phototherapeutic unit 10 can be arranged on the glove 61 or other positions, and it is not limited to be arranged to a single position.

Figure 9:
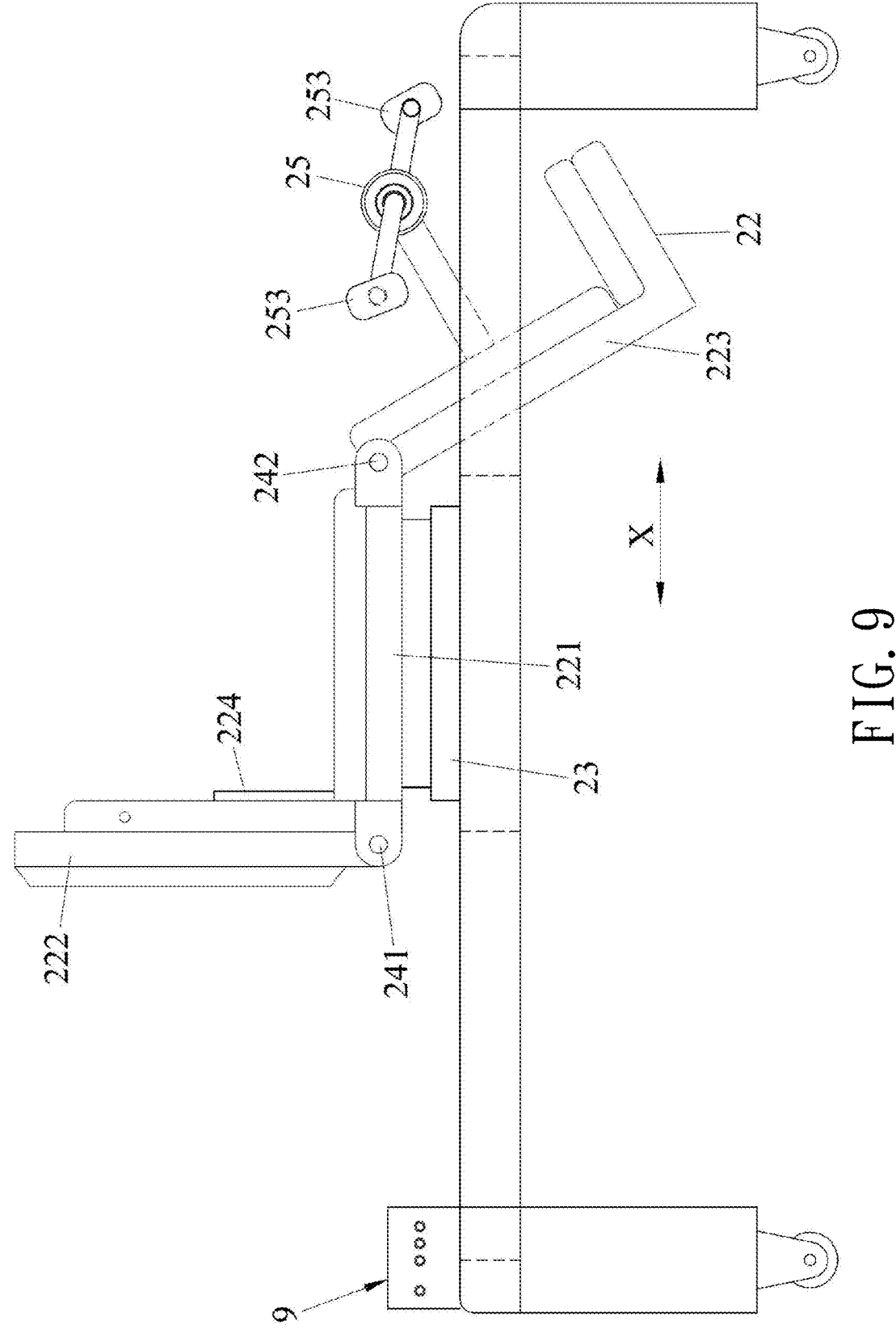
FIG. 9 is a use schematic diagram of a rhythmic bed unit of this embodiment, illustrating a state where an upper body swings upward and a lower body swings downward.

Referring to FIGS. 1 and 9, when in use, a hypertensive patient wears the head frame unit 3 and watches the display module 81, and after wearing the blood pressure measurement module 82, lies flat on the bed module 22, and fixes the hypertensive patient with the fixing waist belt 224. Then, through the display module 81, firstly give a health education film and a static interactive pressure relief self-relaxation exercise film, such as isometric breathing and abdominal breathing. The pulse wave transit time monitoring module 83 measures the transit time of the pulse wave to determine whether the state of self-relaxation is in the state of self-relaxation. If the self-relaxation state has not been reached, the self-relaxation state can be further achieved through film teaching and visual feedback. Then, after stepping on the pedals 253 with both feet, can start to cycle on the pedals 253 for 30 minutes. In the process, the control unit 9 controls the speakers 41 to broadcast the binaural beats with frequency following response for 30 minutes, which can stimulate the neural circuit of the hypertensive patient and train the baroreflex to lower the blood pressure of the hypertensive patient. The display module 81 can also display the blood pressure information measured by the blood pressure measurement module 82 for the user's reference and facilitate the adjustment of the exercise amount.

Figure 10:
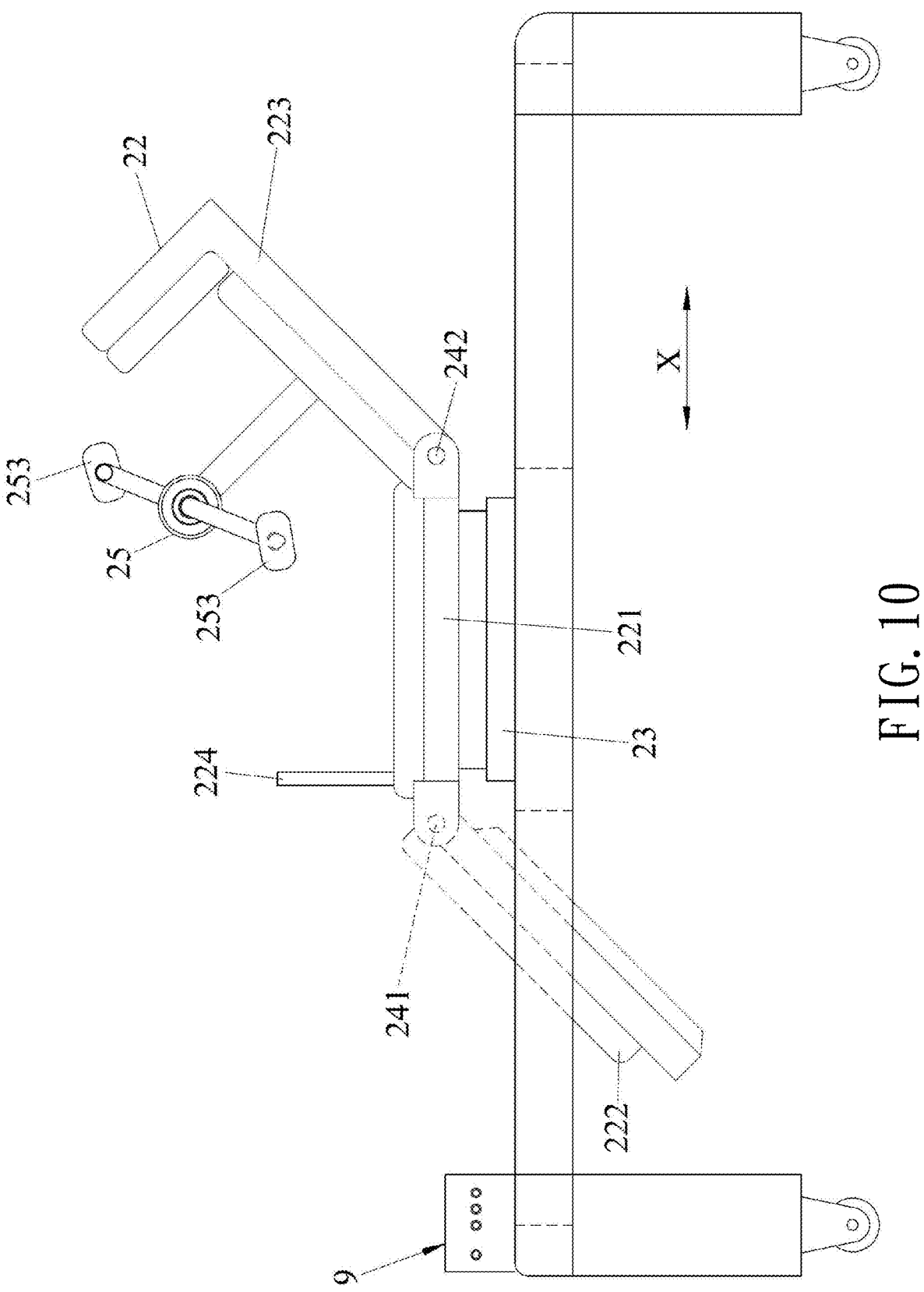
FIG. 10 is a view similar to FIG. 9, illustrating the state where the upper body swings downward and the lower body swings upward.

Further, referring to FIGS. 1, 9 and 10, during the training process, the control unit 9 can further control the first driving member 241 and the second driving member 242 according to the preset command to repeatedly swing the upper body portion 222 and the lower body portion 223 for 10 minutes, that is, when the upper body portion 222 inclines upward, the lower body portion 223 inclines downward (see FIG. 9). When the upper body portion 222 inclines downward, the lower body portion 223 is inclined upward (see FIG. 10), so that the hypertensive patient can swing synchronously in a passive training mode, thus further stimulating the neural circuit of the hypertensive patient and training baroreflex to lower the blood pressure of the hypertensive patient. It should be noted that in human physiology, the arterial baroreflex receptors are mainly located in the aortic arch and carotid sinus. After the pressure receptors in the aortic arch and carotid sinus feel the blood pressure changes (too high or too low), they will be transmitted to the vascular motor center of the medulla oblongata through the tenth pair of vagus nerve and the ninth pair of glossopharyngeal nerve respectively, and then transmitted by sympathetic or parasympathetic nerves to regulate blood pressure. If the blood pressure is kept high, the baroreflex receptor will be mistaken for normal (it is passivated) over time, and the initial heartbeat rate of sympathetic and parasympathetic nerves will not be regulated to decrease, resulting in hypertension, which is caused by long-term factors. Therefore, by tilting and swinging the body, the baroreflex of the human body can be trained.

If the user can't pedal the pedals 253 circularly, the control unit 9 can control the periodic acceleration module 23 to perform horizontal periodic acceleration movement along the head-foot direction X, and lasts for at least 30 minutes according to the preset command when the bed module 22 is adjusted back to the original non-tilted posture. During this process, the blood flow rate of the hypertensive patient is increased due to passive training, which makes the cells release nitric oxide, which can relax the blood vessels and lower the blood pressure of the hypertensive patient, thus completing the complete training process.

Figure 11:
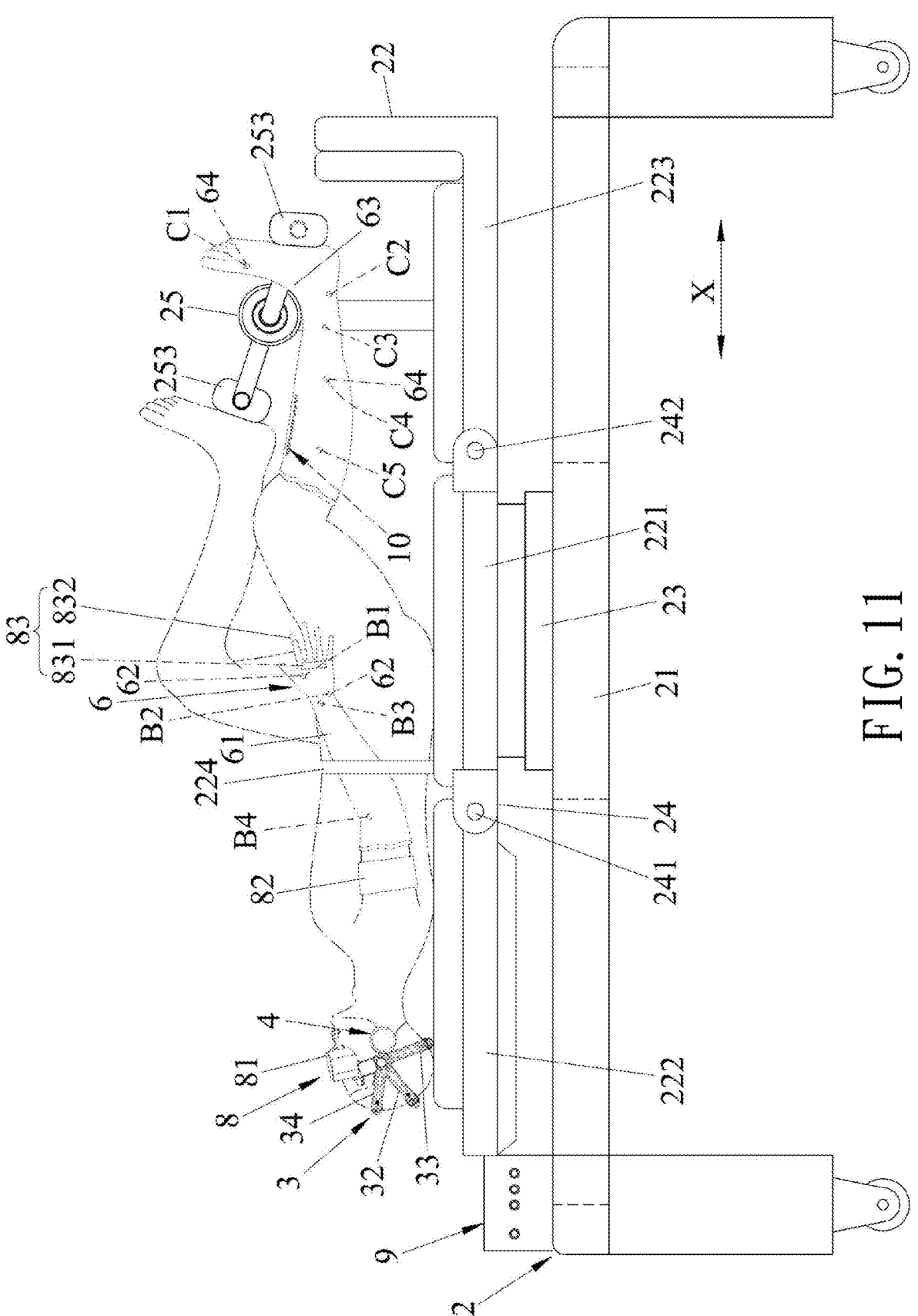
FIG. 11 is a side view of this embodiment, illustrating the state when the user steps on the two pedals.

Referring to FIGS. 2, 5 and 11, if further enhance the training effect, the user can further wear the gloves 61 and the foot cover 63 and lie flat on the bed module 22. Then, the control unit 9 controls the head acupoint agents 51, the hand acupoint agents 62 and the foot acupoint agents 64 to match the corresponding acupoints and output physical stimulation for three to five minutes. At the same time, the control unit 9 controls the electronical stimulation agents 71 to perform physical stimulation for ten to twenty minutes, and at the same time, the control unit 9 controls the speakers 41 to broadcast the binaural beats with frequency following response for thirty minutes, so that the neural circuit of the hypertensive patient can be stimulated and the baroreflex can be trained to lower the blood pressure of the hypertensive patient. It should be noted that, during the physical stimulation of the head acupoint agents 51, when the resistance value is measured by the resistance measuring medium 52 and adjusted to the lowest value, it can be ensured that the head acupoint agents 51 are located on the correct acupoints.

In addition, the flickering picture displayed by the display unit 8 in the optical frequency-flashed stimulation mode and the flickering blue light irradiated by the phototherapeutic unit 10 can further lower the blood pressure of the hypertensive patient.

With the aforementioned training process, the hypertensive patient can perform the exercise of stepping the pedals 253 circularly, receive the stimulation of the binaural beats with frequency following response, the acupoints 51, 62, 64 and the brain regions, tilt the bed module 22 and perform periodic acceleration exercise in one training process, and after different stimulations, the effect of lowering blood pressure can be achieved, which is helpful to improve the symptoms of hypertension after long-term use. Because the blood pressure lowering training equipment provides a very convenient use environment, and enables the hypertensive patients perform training in the form of active exercise or passive exercise, it can effectively improve the willingness for the hypertensive patients to use.

In addition, when the user uses the blood pressure lowering device, the virtual image will produce changes such as landscape changes as the pedals 253 are stepped on, which can make the user feel interesting, so that the user's willingness to use can be greatly improved, and the user can be happy to use it.

Figure 12:
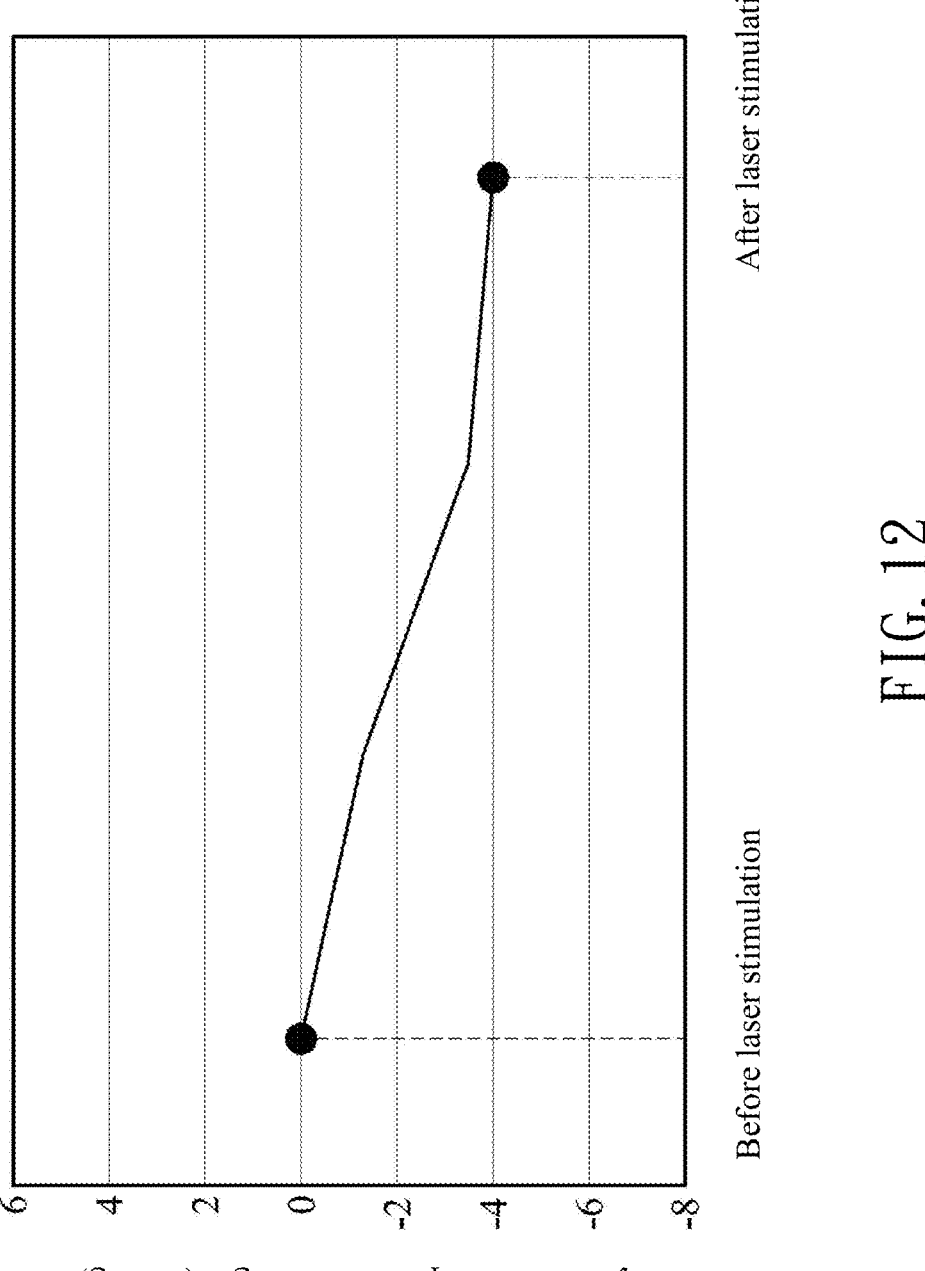
FIG. 12 is a graph showing the change of systolic blood pressure after laser physical stimulation in this embodiment.

Referring to FIGS. 1, 5 and 12, it should be explained that in this embodiment, seven subjects were tested, and the head acupoints (Baihui acupoint A1 and Fengchi acupoint A2) were stimulated through the head acupoint agents 51, the hand acupoints (Hegu acupoint B1, Shenmen acupoint B2 and Quchi acupoint B4) were stimulated through the hand acupoint agents 62, and the foot acupoints (Taichong acupoint C1, Fenglong acupoint C4 and Zusanli C5) were stimulated through the foot acupoint agents 64, from head to toe, each acupoint was stimulated with laser light for 5 minutes, and the results of systolic blood pressure were measured. The results showed that after laser light stimulation, the average systolic blood pressure decreased by about 4 mmHg, and achieve a statistically significant difference, so it can be proved that the physical stimulation of specific acupoints by laser light can achieve the effect of lowering blood pressure.

Next, the results of various experiments are explained. Seven subjects' average systolic blood pressure is about 135 mmHg for periodic accelerated exercise. After a single periodic accelerated exercise through the rhythmic bed unit 2 for 30 minutes, the results of systolic blood pressure changes are measured. The results show that systolic blood pressure decreases by about 9.8 mmHg, diastolic blood pressure decreases by about 5.0 mmHg, and heartbeat decreases by 6.8 beats at rest. The endothelium-dependent vasorelaxation was significantly increased by 5%. Because the periodic accelerated movement of the rhythmic bed unit 2 can increase the flow rate of blood flow and release nitric oxide from cells, it can be proved that the periodic accelerated movement of the rhythmic bed unit 2 can relax the blood vessels, thus lowering the blood pressure of the hypertensive patient.

Then, perform the electronic stimulation experiment with the average systolic blood pressure of seven subjects at about 135 mmHg. After a single transcranial direct current stimulation with a current of 1 mA for 20 minutes, the systolic blood pressure of the subjects was measured. The results showed that the systolic blood pressure decreased by about 4 mmHg, which proved that the physical stimulation of transcranial direct current stimulation could achieve the effect of lowering blood pressure.

Then, perform the audio stimulation experiment with the average systolic blood pressure of seven subjects at about 135 mmHg. After a single beat of the binaural beats with frequency following response with a frequency difference of 4 Hz to 14 Hz for at least 20 minutes, the systolic blood pressure was measured. The results showed that the systolic blood pressure decreased by about 3 mmHg, the heartbeat at rest decreased by 5 beats, the standardized high-frequency power of parasympathetic activity index increased by 4 n.u., and the standardized low-frequency power of sympathetic activity index decreased by 3 n.u.

In addition, the average systolic blood pressure of seven subjects was about 135 mmHg, and the phototherapeutic unit 10 irradiated flashing blue light for optical frequency-flashed stimulation. After a single optical frequency-flashed stimulation for 30 minutes, the results showed that the systolic blood pressure decreased by about 7 mmHg, the diastolic blood pressure decreased by about 5 mmHg, and the endothelium-dependent vasorelaxation was significantly increased by 2%. The results showed that optical frequency-flashed stimulation could accelerate the blood flow rate and promote the cells.

To sum up, by providing the rhythmic bed unit 2 that can swing and perform periodic acceleration movement, the pedal module 25 that can be used for stepping, the speakers 41 that can broadcast the binaural beats with frequency following response, the head acupoint agents 51 that can stimulate acupuncture points, the hand acupoint agents 62 and the foot acupoint agents 64, the electronical stimulation agents 71 that can stimulate brain regions, and the display module 81 that can display the virtual image and blood pressure information, The hypertension patient can carry out a variety of adjustable blood pressure lowering training in one use process, which effectively improves the use intention of the hypertension patient, so that the purpose of the invention can indeed be achieved.

However, the above are only examples of the present invention. While the scope of the present invention cannot be limited by this, all simple and equivalent changes and modifications made according to the patent application scope and the contents of the patent specification of the present invention are still within the scope of the present invention.

What is claimed is:

1. A blood pressure lowering training device, comprising:
a head frame unit corresponds to a user's head shape, and includes two ears corresponding to both ears of the user, a top-side portion connected between the ears and spanning the user's head;
an audio stimulation unit includes two speakers arranged at the ears, and the speakers are used to broadcast binaural beats with frequency following response to both ears of the user, and the binaural beats between the two ears have a frequency difference;
a display unit includes a display module arranged on the front-side of the head frame unit to display a virtual image for the user's eyes, a blood pressure measurement module for measuring the user's blood pressure and outputting the measurement result by signal, the display module is configured to also display the blood pressure information measured by the blood pressure measurement module;
a control unit is electrically connected with the speakers and the display unit, stores digital information of the binaural beats with frequency following response, and is configured to control the speakers to broadcast the binaural beats with frequency following response according to a preset command, and change the virtual image in the display module; and
a head acupoint stimulation unit, wherein the top-side portion having a top area located at the center between the ears, and the head acupoint stimulation unit comprises three head acupoint agents which are arranged in the head acupoint stimulation unit, are electrically connected and configured to be controlled by the control unit to give physical stimulation according to the preset command, the head acupoint agents are used to output the physical stimulation of laser light to the user's head acupoints, and one of the head acupoint agents is adjustably arranged in the center of the top area to correspond to the Baihui acupoint of the user.

2. The blood pressure lowering training device according to claim 1, wherein the frequency difference of binaural beats is from 4 Hz to 14 Hz.

3. The blood pressure lowering training device according to claim 1, wherein the head frame unit further comprises a back-side portion connected between the ears and spanning the user's back skull, two of the head acupoint agents are adjustably arranged at the back-side portion, and located seven times rearward of the center of the top area, and are separated from the ears by 2.25 times of the finger distance to respectively correspond to the two Fengchi acupoints of the user, and the finger distance is substantially 2.3 cm, the wavelength of the laser light of the head acupoint agents 51 is between 500 nm and 900 nm.

4. The blood pressure lowering training device according to claim 3, the three head acupoint agents are electrically connected to the control unit and adjacent to the head acupoint agents, respectively, and each resistance measuring medium is used to measure the body resistance of the user to confirm whether the corresponding head acupoint agents is located in a low resistance acupoint area.

5. The blood pressure lowering training device according to claim 3, further including a limb acupoint stimulation unit, and the limb acupoint stimulation unit includes a glove, four hand acupoint agents which electrically connected to the control unit and disposed on the glove, the hand acupoint agents is used to output physical stimulation of laser light to the user's hand acupoint, one of the hand acupoint agents is configured to adjustably correspond to Hegu acupoint of the user, and one of the hand acupoint agents is configured to adjustably correspond to Shenmen acupoint of the user, one of the hand acupoint agents is configured to adjustably correspond to the user's Neiguan-acupoint, and one of the hand acupoint agents is configured to adjustably correspond to the user's Quchi acupoint, the laser wavelengths of the hand acupoint agents are between 500 nm and 900 nm.

6. The blood pressure lowering training device according to claim 3, the limb acupoint stimulation unit further includes a foot cover, five foot acupoint agents which electrically connected to the control unit and disposed on the foot cover, the foot acupoint agents is used to output physical stimulation of laser light to the user's foot acupoint, one of the foot-acupoint agents is configured to adjustably correspond to the user's Taichong acupoint, and one of the foot acupoint agents is configured to adjustably correspond to the user's Taixi-acupoint, one of the foot-acupoint agents is configured to adjustably correspond to the user's Sany-injiao-acupoint, one of the foot-acupoint agents is configured to adjustably correspond to the user's Fenglong-acupoint, and one of the foot acupoint agents is configured to adjustably correspond to the user's Zusanli-acupoint, the laser wavelengths of the foot acupoint agents are between 500 nm to 900 nm.

7. The blood pressure lowering training device according to claim 1, further including an electronical stimulation agents, and the head frame unit further comprises a front-side portion connected between the ears, spanning the forehead of the user and connected to the display unit, and an middle portion connected between the ears and located between the top-side portion and the front-side portion, wherein a left side area and a right side area connected to the ears and the top area respectively, the middle portion has a left front area corresponding to the left side area, and the electronic stimulation unit includes three electronical stimulation agents corresponding to the left side area, the left front area and the front-side portion area respectively, which are electrically connected and configured to be controlled by the control unit to emit physical stimulation according to the preset command, and these electronical stimulation agents correspond to the C3 position, F3 position and SO position in the international 10-20 system electroencephalogram electrode positions, respectively, and it is used for physical stimulation of one of outputting current to the user's head for transcranial electrical stimulation and outputting electromagnetic pulses for transcranial magnetic stimulation.

8. The blood pressure lowering training device according to claim 7, wherein when the electronical stimulation agents output direct current, the current magnitude is between 1 mA and 2 mA, and the current density is between 0.03 mA/cm$^2$ and 0.09 mA/cm$^2$, and when the electronical stimulation agents output electromagnetic pulse, the electromagnetic frequency is substantially 1 Hz.

9. The blood pressure lowering training device according to claim 7, wherein each electronical stimulation agents has several conductive columns arranged in parallel to output physical stimulation, and two of these electronical stimulation agents respectively corresponding to C3 position and F3 position in the international 10-20 electroencephalogram electrode position are anodes, and one of these electronical stimulation agents corresponding to SO position in the international 10-20 electroencephalogram electrode position is cathodes.

10. The blood pressure lowering training device according to claim 7, wherein the top-side portion further has a first mounting slot located in the left side area, and the middle portion also has a second mounting slot located in the left front area, and the electronic stimulation unit further comprises a first setting base and a second setting base, the first setting base has a first sliding member arranged at the bottom of the top-side portion, a first screw lock member that passes through the first mounting slot from the side opposite to the first sliding member and is screwed to the first sliding member to fix the first sliding member, a first positioning member that slidably passes through the first screw lock member from the side opposite to the first sliding member, a first mounting platform which is arranged on the side of the first sliding member opposite to the top-side portion and screwed to the first positioning member a plurality of first conductive member arranged at the bottom of the top-side portion, and a plurality of first elastic conductive strips which are configured to compressively pass through the first sliding member and the first mounting platform and are electrically connected to the first conductive strips respectively, the electronical stimulation agents corresponding to the left side area is arranged on the side of the first mounting platform opposite to the top-side and electrically connected to the first elastic conductive member, the second setting base has a second sliding member arranged at the bottom of the middle portion, a second screw locking member which passes through the second mounting slot from the side opposite to the second sliding member in the middle portion and is screwed to the second sliding member for fixing the second sliding member, a second positioning member which slidably passes through the second screw locking member from the side opposite to the second sliding member, a second mounting platform which is arranged on the side of the second sliding member opposite to the middle portion and screwed to the second positioning member, a plurality of second conductive strips arranged at the bottom of the middle portion, and a plurality of second elastic conductive members are configured to compressively pass through the second sliding member and the second mounting platform and are electrically connected with the second conductive strips respectively, and the electronical stimulation agents corresponding to the left front area are arranged on the side of the second mounting platform opposite to the middle portion and electrically connected with the second elastic conductive members.

11. The blood pressure lowering training device according to claim 1, further comprising a rhythmic bed unit, which comprises a base, a bed module arranged on the base, a periodic acceleration module arranged between the base and the bed module, a driving module arranged on the bed module, and a pedal module arranged on the bed module, the bed module has a middle portion arranged above the base, an upper body portion swingably arranged at the head-side of the middle portion along the head-foot direction, and a lower body portion swingably arranged at the foot-side of the middle portion along the head-foot direction, the periodic acceleration module is arranged between the base and the middle portion and configured to be controlled to drive the middle portion to move headward and footward along the head-foot horizontal direction, the driving module has a first driving member which is arranged between the middle portion and the upper body portion and configured to be controlled to drive the upper body portion to swing relative to the middle portion, and a second driving member which is arranged between the middle portion and the lower body portion and configured to be controlled to drive the lower body portion to swing relative to the middle portion, pedal module has a supporting portion arranged on the lower body portion, a crank pivoted on the supporting portion, two pedals respectively arranged on two opposite sides of the crank, a sensor arranged on the crank and outputting the rotation of the crank into a sensing signal, wherein the periodic acceleration module, the driving module and the sensor are electrically connected with the control unit, and the control unit is configured to control the periodic acceleration module to perform periodic acceleration movement and the driving module to drive the upper body portion and the lower body to swing according to the preset command, and the control unit is configured to receive and change the virtual image on the display module according to the sensing signal.

12. The blood pressure lowering training device according to claim 11, wherein the bed module further has a fixed waist belt arranged at the middle portion.

13. The blood pressure lowering training device according to claim 11, wherein the swing angle at which the first driving member drives the upper body portion to swing relative to the middle portion is between a horizontal upward 90 degrees angle and a horizontal downward 45 degrees angle, and the swing angle at which the second driving member drives the lower body portion to swing relative to the middle portion is between a horizontal upward 45 degree angle and a horizontal downward 45 degree angle.

14. The blood pressure lowering training device according to claim 1, wherein the display unit further comprises a pulse wave transit time monitoring module for measuring the transit time of the pulse wave of the user, and the display module is configured to also display the transit time of the pulse wave measured by the pulse wave transit time monitoring module.

15. The blood pressure lowering training device according to claim 1, wherein the display unit is configured to be switched between a display mode and an optical frequency-flashed stimulation mode, in the display mode, the display module displays the virtual image for the eyes of the user, and in the optical frequency-flashed stimulation mode, the display module stimulates the eyes of the user with flickering flash.

16. The blood pressure lowering training device according to claim 15, wherein when the display unit is in the optical frequency-flashed stimulation mode, the flickering flash displayed by the display module flickers with no-ultraviolet blue light with a wavelength between 450 nm to 465 nm.

17. The blood pressure lowering training device according to claim 1, further comprising a phototherapeutic unit electrically connected to the control unit, and the phototherapeutic unit is used for emitting no-ultraviolet flashing blue light with a wavelength between 450 nm and 465 nm to the user.

18. The blood pressure lowering training device according to claim 1, wherein the digital information, the virtual image and the preset command are downloaded through the cloud network and then pre-stored in the control unit.

* * * * *